(12) United States Patent
Oscarsson et al.

(10) Patent No.: US 9,777,075 B2
(45) Date of Patent: Oct. 3, 2017

(54) DIAGNOSTIC ASSAY USING PARTICLES WITH MAGNETIC PROPERTIES

(71) Applicant: Lab-on-a-bead AB, Lycke (SE)

(72) Inventors: Sven Oscarsson, Uppsala (SE); Kristofer Eriksson, Strängnäs (SE); Peter Svedlindh, Uppsala (SE)

(73) Assignee: Lab-on-a-bead AB, Lycke (SE)

( * ) Notice: Subject to any disclaimer, the term of this patent is extended or adjusted under 35 U.S.C. 154(b) by 0 days.

(21) Appl. No.: 15/064,815

(22) Filed: Mar. 9, 2016

(65) Prior Publication Data

US 2016/0187327 A1    Jun. 30, 2016

Related U.S. Application Data

(63) Continuation of application No. PCT/SE2014/051037, filed on Sep. 9, 2014.

(30) Foreign Application Priority Data

Sep. 9, 2013 (SE) ..................... 1351038

(51) Int. Cl.
| | | |
|---|---|---|
| G01N 33/548 | (2006.01) | |
| C08B 37/00 | (2006.01) | |
| B01J 20/285 | (2006.01) | |
| B01J 20/286 | (2006.01) | |
| B01J 20/32 | (2006.01) | |

(Continued)

(52) U.S. Cl.
CPC ......... *C08B 37/0039* (2013.01); *B01J 20/24* (2013.01); *B01J 20/285* (2013.01); *B01J 20/286* (2013.01); *B01J 20/28009* (2013.01); *B01J 20/28016* (2013.01); *B01J 20/321* (2013.01); *B01J 20/3204* (2013.01); *B01J 20/3212* (2013.01); *B01J 20/3217* (2013.01); *B01J 20/3242* (2013.01); *B01J 20/3265* (2013.01); *G01N 33/548* (2013.01); *G01N 33/5434* (2013.01);
(Continued)

(58) Field of Classification Search
CPC ............ C08B 37/0039; B01D 15/3885; B01D 15/3804
USPC .......................................... 506/9
See application file for complete search history.

(56) References Cited

U.S. PATENT DOCUMENTS 7,897,257 B2 * 3/2011 Alterman ......... G01N 33/54326
                                                           427/127
2005/0196856 A1    9/2005 Harrold et al.
(Continued)

FOREIGN PATENT DOCUMENTS

CN    102703411 A  * 10/2012
WO    95/03356 A1    2/1995
(Continued)

OTHER PUBLICATIONS

International Search Report for co-pending International Application No. PCT/SE2014/051034 dated Dec. 17, 2014.
(Continued)

*Primary Examiner* — Karla Dines
(74) *Attorney, Agent, or Firm* — Renner, Otto, Boisselle & Sklar, LLP

(57) ABSTRACT

A novel system for the analysis of molecules and cells, comprising clusters where a non-magnetic particle is supplemented with magnetic particles to form a characteristic pattern, fingerprint or bar code. Methods and devices for formation of such particles are also disclosed.

5 Claims, 4 Drawing Sheets

(51) Int. Cl.
*B01J 20/28* (2006.01)
*B01J 20/24* (2006.01)
*G01N 33/543* (2006.01)
*B01D 15/38* (2006.01)

(52) U.S. Cl.
CPC ...... *B01D 15/3804* (2013.01); *B01D 15/3885* (2013.01)

(56) References Cited

U.S. PATENT DOCUMENTS

2012/0037840 A1  2/2012  Stucky et al.
2013/0197195 A1  8/2013  Oscarsson et al.

FOREIGN PATENT DOCUMENTS

| WO | 2006/017428 A2 | 2/2006 |
| WO | 2009/131526 A1 | 10/2009 |
| WO | 2009/151490 A2 | 12/2009 |
| WO | 2012/013693 A1 | 2/2012 |
| WO | 2013/187831 A1 | 12/2013 |

OTHER PUBLICATIONS

Written Opinion of the International Search Authority for co-pending International Application No. PCT/SE2014/051034 dated Dec. 17, 2014.
International Preliminary Report on Patentability for co-pending International Application No. PCT/SE2014/051034 dated Jul. 6, 2016.
International Search Report for co-pending International Application No. PCT/SE2014/051036 dated Dec. 17, 2014.
Written Opinion of the International Search Authority for co-pending International Application No. PCT/SE2014/051036 dated Dec. 16, 2014.
International Preliminary Report on Patentability for co-pending International Application No. PCT/SE2014/051036 dated Dec. 16, 2014.
International Search Report for co-pending International Application No. PCT/SE2014/051037 dated Dec. 19, 2014.
Written Opinion of the International Search Authority for co-pending International Application No. PCT/SE2014/051037 dated Dec. 19, 2014.
International Preliminary Report on Patentability for co-pending International Application No. PCT/SE2014/051037 dated Dec. 18, 2014.
Safarik et al., "Large-scale separation of magnetic bioaffinity adsorbents", Biotechnology Letters 23, 2001, pp. 1953-1956.
Berensmeier, "Magnetic particles for the separation and purification of nucleic acids", Applied Microbiology and Biotechnology, vol. 73, Issue 3, Dec. 2006, pp. 495-504.
English translation of Office Action received in co-pending Chinese Application No. 2014800590596 dated Apr. 7, 2017.

\* cited by examiner

DIAGNOSTIC ASSAY USING PARTICLES WITH MAGNETIC PROPERTIES

This application is a continuation of international Application No. PCT/SE2014/051037, filed 9 Sep. 2014, which claims priority to Swedish patent application SE 1351038-3, filed 9 Sep. 2013, the entire contents of which are hereby incorporated by reference.

TECHNICAL FIELD

The present description relates generally to a novel system for analysis of molecules and cells, comprising clusters where a non-magnetic particle is supplemented with magnetic particles to form a characteristic pattern or bar codes. Such particles and methods for their production are also disclosed.

BACKGROUND

Techniques for the analysis of biomolecules and cells in body fluids are of crucial importance in many technical fields, such as but not limited to medicine, biopharmacy and biotechnology. Traditional immunological techniques such as enzyme-linked immunosorbent assays (ELISA) are still predominant. However, as the number of analysis performed worldwide is constantly increasing, the need for faster and more efficient methods for analysis becomes crucial. Systems relying on multiplex analysis represent one solution to more efficient analytical systems. Several commercial techniques using multiplexing are now available. The existing multiplex analysis systems however have many disadvantages. Among these, the high cost for instrumentation and the evaluation of the results should be mentioned.

There is also a need of miniaturization of components within nanotechnology, diagnosis, research and development. Within many areas there is a need to store information or attach various molecules on a particle.

There are known technologies to store information on larger particles and to derivatize large particles. Regarding partial derivatization of smaller particles, such as particles with a diameter below 100 μm, technical problems arise. One problem is the control of the particle movement. Thus there is a need in the art for a method to manufacture partially derivatized smaller particles.

One example is the method for partially derivatizing a curved surface of particles in an electrically conducting solvent, disclosed in WO2009074692. Said method comprises the steps: a) bringing particles in close contact with at least one surface by using a force, b) inducing a chemical reaction on at least one part of a particle by applying an electrical potential between said at least one surface and the electrically conducting solvent, and c) further reacting said at least one part of a particle where a chemical reaction has been induced in step b) above. WO2009074692 also discloses a partially derivatized particle as well as uses of said particle.

SUMMARY

It is an object of the general concept and embodiments set out herein to alleviate at least some of the disadvantages of the prior art and to provide an improved material for analysis, said material comprising particles where a porous particle is supplemented with magnetic particles on the surface of the porous particles where the magnetic particles not only contribute with magnetic elements, and their magnetic force, but are also creating characteristic patterns or bar codes which are also possible to use for immobilization of ligands leaving the majority of the inner space of the porous particle unaffected by the magnetic particles and maintaining or even increasing capacity of the particle compared to known magnetic particles and particle aggregates.

A first aspect concerns a method for the production of particles, said method comprising the steps of:

a. providing non-magnetic porous particles having an exterior surface, pores and a connected interior surface defined by said pores, the porous particles comprising at least one polymer, the porous particles comprising at least one type of functional groups on said exterior and interior surfaces, and magnetic particles comprising at least one type of functional groups on their surface, wherein the smallest diameter of at least 95 percent per weight of the magnetic particles is larger than the average diameter of the pores of the porous particles; and b. reacting functional groups on the surface of the non-magnetic porous particle, with functional groups on the surface of the magnetic particles to form a covalent bond, to obtain particles supplemented with magnetic particles covalently bound to the outer part of the particles.

By selecting magnetic particles of different size, color and magnetic properties, the particles are given unique identifiers, comparable to a characteristic pattern, fingerprint or bar code.

In an embodiment of the first aspect the porous particle comprises a material selected from the group consisting of agarose, silica, cellulose, poly vinyl alcohols, polyethylene glycols, polystyrene, and derivatives thereof.

In another embodiment of the first aspect the magnetic particles have a density which is higher than the density of the non-magnetic porous particle.

In one embodiment the smallest diameter of at least 95 percent per weight of all magnetic particles is larger than the largest diameter of at least 95% of all pores of the porous particles.

The smallest diameter of at least 95 percent per weight of all magnetic particles describes the smallest of all possible diameters of at least 95 percent per weight of all magnetic particles. Weight percentage and not number is used to reduce the relative weight of very small particles.

The average diameter of the pores of the porous particles is measured and defined as the apparent pore dimensions as further detailed in Hagel, Östberg, Andersson in Journal of Chromatography A, Volume 743, issue 1, 30 Aug. 1996, pages 33-42. There is also data for some commercially available polymers. For instance the average, or apparent, pore diameter in 6% agarose is 24 nm.

When the smallest diameter of almost all, preferably at least 95 percent per weight, of all magnetic particles is larger than the average diameter of the pores of the porous particles, the magnetic particles can enter the porous particles to some extent, but not to such an extent that the magnetic particles block the binding capacity of the porous particles or the possibility to identify the bar code. By allowing the magnetic particles to enter the porous particles to some extent the total binding capacity of the particles can actually increase, since the magnetic particles present functional groups on their surface which can be utilized to increase the binding capacity or to create the bar codes either directly or by further reaction to bind other molecules. By allowing a fraction of the magnetic particles to enter the particles, the load of magnetic material is increased, which makes the particles more useful for separation, since it is easier to separate them if they have more magnetic material in them.

For many applications, in particular for separation a high magnetic moment is desired for the particle. Also the binding capacity of the particle should be high. This is solved in such a fashion, that the magnetic particles are possible to derivatize with functional groups so that they contribute to the total binding capacity of the particle. Both the binding capacity of the particle and the magnetic moment is maximized by allowing some magnetic particles to enter the porous particle and by derivatizing the magnetic particles with functional groups that contribute to the total binding capacity of the particle and to optimize the creation of bar codes In one embodiment the magnetic particles are 20 nm or larger. In one embodiment the magnetic particles are 4 or smaller. In an alternative embodiment the magnetic particles are 100 nm or smaller. In one embodiment a stable colloid of magnetic particles is utilized during the manufacturing process. The diameter of individual magnetic particles is used, if the magnetic particles form clusters the largest diameter of the entire cluster can be considerably larger It is conceived that even if the manufacturing processes are satisfactory there may be a few particles which are smaller or larger than the intended size in a practical manufacturing process.

In an alternative embodiment, the smallest diameter of the magnetic particles is equal or smaller than the average diameter of the pores of the porous particle. In this embodiment, at least a portion of the magnetic particles will enter into the pores of the porous particle. By choosing the size of the magnetic elements in relation to the pore size, the magnetic load can be adapted as desired.

The smallest diameter of the magnetic particles is larger than the average diameter (apparent diameter) of the pores of the porous particle. It is intended that the smallest diameter of the magnetic particles means the smallest diameter of essentially all, or preferably at least 95 percent per weight, of the magnetic particles, where smallest diameter is measured in a dimension where the size of the particle is smallest. In such an alternative embodiment essentially all magnetic particles are too large to enter in an average pore of the porous particle. It is conceived that the pore size can vary and will have a certain size distribution, and some pores are accessible for the magnetic particles in such an embodiment.

In yet an alternative embodiment the smallest diameter of the magnetic particles is larger than the diameter of all pores of the porous particle. In such an embodiment no pores are accessible for the magnetic particles.

For some diagnostic applications it is desired that magnetic particles are only present on the exterior surface of the porous particles.

In another embodiment of the first aspect the functional groups on the exterior and interior surfaces the porous particle are selected from the group consisting of —SH, —S—S-pyridin, —COOH, —NH$_2$, —CHO, —OH, phenol, anhydride, epoxy, S—Au, and amide, amino ethyl, diethyl aminoethyl, quaternary aminoethyl, carboxymethyl, phosphopropyl and sulfopropyl.

In another embodiment of the first aspect the functional groups on the exterior and interior surfaces of the porous particle include at least one group which is the result of a reaction with at least one compound selected from the group consisting of divinylsulfone, benzoquinone, imidazol, periodate, trichloro-S-triazine, tosylates, diazonium, isourea salts, carbodiimides, hydrazine, epichlorohydrin, glutaraldehyd, cyanogenbromide, bisepoxiranes, carbonyldiimidazol, N-hydroxysuccinimid, silanes and derivatives thereof.

In another embodiment of the first aspect the functional groups on the magnetic particles include at least one selected from the group consisting of —SH, —S—S-pyridin, —COOH, —NH$_2$, —CHO, —OH, phenol, anhydride, epoxy, S—Au, and amide, amino ethyl, diethyl aminoethyl, quaternary aminoethyl, carboxymethyl, phosphopropyl and sulfopropyl.

In another embodiment of the first aspect the functional groups on the surface of the magnetic particles include at least one which is the result of a reaction with at least one compound selected from the group consisting of divinylsulfone, benzoquinone, imidazol, periodate, trichloro-S-triazine, tosylates, diazonium, isourea salts, carbodiimides, hydrazine, epichlorohydrin, glutaraldehyd, cyanogenbromide, bisepoxiranes, carbonyldiimidazol, N-hydroxysuccinimid, silanes and derivatives thereof.

In another embodiment of the first aspect molecules adapted for molecular interactions are introduced on either the porous particles, the magnetic particles, or on both.

In a further embodiment of the first aspect the molecule adapted for molecular interaction is at least one selected from the group consisting of an organic molecule, a protein, an antigen, an enzyme, an enzyme inhibitor, a cofactor, a hormone, a toxin, a vitamin, a glycoconjugate, a nucleic acid, a lectin, and a carbohydrate.

In another embodiment of the first aspect, freely combinable with the above embodiments, molecules adapted for detection are introduced on at least one selected from the group consisting of the porous particles and the magnetic particles.

In another embodiment of the first aspect, freely combinable with the above embodiments, the molecule adapted for detection is at least one selected from the group consisting of an organic molecule, a nucleic acid, an amino acid, a peptide, a protein and a lectin.

In another embodiment of the first aspect, freely combinable with the above embodiments, the magnetic particles comprise particles of at least one magnetic material embedded in a polymer matrix, and wherein said polymer matrix comprises the functional groups.

A second aspect concerns a particle comprising a non-magnetic porous particle having an exterior surface, pores and an interior surface defined by said pores, the porous particles comprising at least one polymer, said particle having at least one magnetic particle covalently bound to the outer parts thereof, wherein the smallest diameter of at least 95 percent per weight of the magnetic particles is larger than the average diameter of the pores of the porous particles.

According to an embodiment of the second aspect, the porous particle comprises at least one material selected from the group consisting of agarose, silica, cellulose, polyvinyl alcohols, polyethylene glycols, polystyrene, and derivatives thereof.

According to a further embodiment of the second aspect, the magnetic particles have a density which is higher than the density of the non-magnetic porous particle.

According to a further embodiment of the second aspect, freely combinable with the above embodiments, at least one selected from the group consisting of the porous particle and the at least one magnetic particle comprise molecules adapted for molecular interactions.

According to a further embodiment of the second aspect, freely combinable with the above embodiments, at least one selected from the group consisting of the porous particle and the at least one magnetic particle comprise molecules adapted for detection.

According to a further embodiment of the second aspect, freely combinable with the above embodiments, the molecules adapted for detection is at least one selected from the group consisting of an organic molecules, a nucleic acid, an antigen, an enzyme, an enzyme inhibitor, a co-factor, a hormone, a toxin, a glycoconjugate, a lectin, and a carbohydrate.

According to a further embodiment of the second aspect, freely combinable with the above embodiments, the magnetic particles comprise particles of at least one material embedded in a polymer matrix, and wherein said polymer matrix comprises the functional groups.

A method for performing an assay using particles, comprising the steps of:
- contacting the particles with a sample comprising at least one analyte to be analysed wherein the particles have an affinity for said analyte,
- bring the particles in contact with a surface on which molecules which have bioaffinity for the analyte immobilised to particle are immobilised
- exposing the particles to at least one of i) a magnetic field, ii) gravity, and iii) centrifugation followed by rinsing surface from non-specifically bound particles
- reading a detectable signal from the particles which are immobilised to surface.

The method, wherein the assay is a multiplex assay involving the use of subgroups of particles wherein the porous particles in each subgroup carry magnetic particles of different size.

The method, wherein the assay is a multiplex assay involving the use of subgroups of particles wherein the porous particles in each sub-group carry magnetic particles of different color and or size.

An advantage of this method is that all steps during the preparation of the particles are easy to perform even in aqueous solutions and at moderate temperatures, for example at about 20-60° C.

Another advantage is that the covalent bonds formed during the reactions involving the groups on the surface and inside the porous particle are stable, even for single point attached molecules.

Yet another advantage is that the method can be performed with very few steps. The method is easier to perform compared to methods according to the prior art and with simple inexpensive equipment.

Particles according to aspects and embodiments described herein have several advantages. Not only is it possible to design particles that are easily identifiable due to a characteristic pattern, fingerprint or bar code, the particles also have an increased binding capacity compared to known magnetic particles. The binding capacity is maintained and/or even improved by formation of a particle supplemented with magnetic particles on which ligands can also be immobilised leaving the main part of the inner volume of the porous particle unaffected and available to adsorption and binding reactions with the component to be separated. Since a porous particle has most of its specific surface area on the interior, the reaction and/or adsorption capacity will be maintained if the magnetic particles are not too small and not blocking the pores of the porous particle.

BRIEF DESCRIPTION OF THE DRAWINGS

Aspects and embodiments will be described with reference to the following drawings in which.

DETAILED DESCRIPTION

Figure 1:
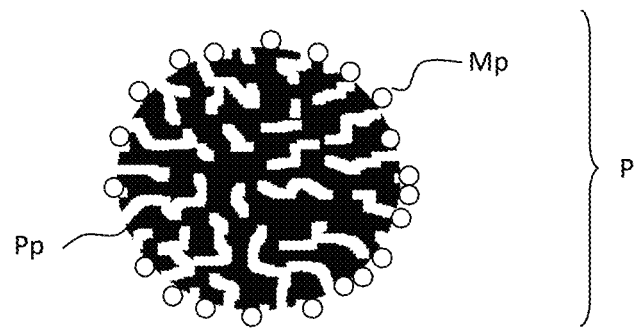
FIG. 1 schematically shows a cross-section of a particle (P) comprising a porous non-magnetic particle (Pp) and multiple magnetic particles (Mp) distributed over its surface.

Before describing various aspects and embodiments in detail, it is to be understood that this description is not limited to particular compounds, configurations, method steps, substrates, and materials disclosed herein as such compounds, configurations, method steps, substrates, and materials may vary somewhat. It is also to be understood that the terminology employed herein is used for the purpose of describing particular embodiments only and is not intended to be limiting since the scope of the present embodiments is limited only by the appended claims and equivalents thereof.

It must be noted that, as used in this specification and the appended claims, the singular forms "a", "an" and "the" include plural referents unless the context clearly dictates otherwise.

Also, the term "about" is used to indicate a deviation of ±10%, and most preferably ±5% of the numeric values, where applicable.

As used throughout the description and the claims, the diameter of a sphere is any straight line that passes through the center of the sphere, having endpoints on the periphery of the sphere.

If nothing else is defined, the scientific terminology including any terms used herein are intended to have the meanings commonly understood by those of skill in the art to which this disclosure pertains.

The inventors have carried out extensive research and found that the particles defined in the claims are easy to form with high yield and easy to separate. The capacity to bind biomolecules to the cluster and to isolate biomolecules from the cluster was found to be higher than any published data for corresponding particles according to the state of the art.

Particles according to an embodiment are magnetic and easy to use in processes for detection of biomolecules. The particles together with immobilized molecules and/or cells are easily separated using external magnets. They are also easily identifiable thanks to the characteristic pattern, fingerprint or bar code given to them by the combination of magnetic particles of different size and properties. Further, as the magnetic particles give added density to the particles, the separation can be aided by centrifugation or by static settling using gravity. Density-based separation can be used as a pre-separation step and/or as part of the magnetic separation.

A first aspect provides a method for the production of particles, said method comprising the steps of:
a. providing
   non-magnetic porous particles having an exterior surface, pores and a connected interior surface defined by said pores, the porous particles comprising at least one polymer, the porous particles comprising functional groups on said exterior and interior surfaces, and
   magnetic particles comprising functional groups on their surface, wherein the smallest diameter of at least 95 percent per weight of the magnetic particles is larger than the average diameter of the pores of the porous particles; and
b. reacting the functional groups on the surface of the non-magnetic porous particle, with the functional groups on the surface of the magnetic particles to form a covalent bond,
to obtain particles supplemented with magnetic particles covalently bound to the outer part of the particles, Preferably all of the at least one type of functional groups on the surface of the magnetic particles have not reacted to form covalent bonds with the at least one type of functional groups on the exterior and interior surfaces of the porous particles so that a fraction of the at least one type of functional groups remain available on at least one selected from the magnetic particles and the porous particles The resulting particles can be considered as surface decorated porous particles, where magnetic particles are bound to the surface and outer part of the particle.

According to one embodiment the porous particles are essentially spherical, however also other shapes are encompassed and the porous particles are not limited to any specific shape. All shapes are encompassed within the scope of the embodiments presented herein. The same applies to the magnetic particles.

When the smallest diameter of almost all, preferably at least 95 percent per weight, of all magnetic particles is larger than the average diameter of the pores of the porous particles, the magnetic particles can enter the porous particles to some extent, but not to a so large extent that the magnetic particles block the capacity of the porous particles or makes it difficult to read the bar code. By allowing the magnetic particles to enter the porous particles to some extent the total binding capacity of the particles can actually increase, since the magnetic particles have available functional groups on their surface which can be utilized to increase the binding capacity either directly or by further reaction to bind other molecules. By allowing a fraction of the magnetic particles to enter the load of magnetic material is increased in the particles, which makes the particles more useful for separation, since it is easier to separate them if they have more magnetic material in them.

For many applications, in particular for separation a high magnetic moment is desired for the particle. Also the binding capacity of the particle P should be high. This is solved so that the magnetic particles are possible to derivatize with functional groups so that they contribute to the total binding capacity of the particle. Both the binding capacity of the particle and the magnetic moment is maximized by allowing some magnetic particles to enter the porous particle and by derivatizing the magnetic particles with functional groups that contribute to the total binding capacity of the particle.

In one embodiment the magnetic particles are 20 nm or larger. In one embodiment the magnetic particles are 4 µm or smaller. In an alternative embodiment the magnetic particles are 100 nm or smaller. In one embodiment a stable colloid of magnetic particles is utilized during the manufacturing process. The diameter of individual magnetic particles is used, but if the magnetic particles form clusters the largest diameter of the entire cluster can be considerably larger.

It is conceived that even if the manufacturing processes are satisfactory there may be a few particles which are smaller or larger than the intended size in a practical manufacturing process.

In an alternative embodiment, the smallest diameter of the magnetic particles is equal or smaller than the average diameter of the pores of the porous particle. In this embodiment, at least a portion of the magnetic particles will enter into the pores of the porous particle. By choosing the size of the magnetic elements in relation to the pore size, the magnetic load can be adapted as desired.

The smallest diameter of the magnetic particles is larger than the average diameter (apparent diameter) of the pores of the porous particle. It is intended that the smallest diameter of the magnetic particles means the smallest diameter of essentially all, preferably at least 95 percent per weight, of the magnetic particles, where the smallest diameter is measured in a dimension where the size of the particle is smallest. In such an alternative embodiment essentially all magnetic particles are too large to enter into an average pore of the porous particle. It is conceived that the pore size can vary and will have a certain size distribution, and some pores are accessible for the magnetic particles in such an embodiment.

In yet an alternative embodiment the smallest diameter of the magnetic particles is larger than the diameter of all pores of the porous particle. In such an embodiment no pores are accessible for the magnetic particles.

For some diagnostic applications it is desired that magnetic particles are only present on the exterior surface of the porous particles.

According to one embodiment the porous particles are essentially spherical, however also other shapes are encompassed and the porous particles are not limited to any specific shape. All shapes are encompassed within the scope of the embodiments presented herein. The same applies to the magnetic particles.

For a spherical or an essentially spherical particle the diameter is easy to determine according to the usual definition. For a perfectly spherical particle the smallest and the largest diameter are the same. However for irregularly shaped particles, i.e. non-spherical particles, the diameter can be measured in many different directions from one point on the surface through the center of mass to another point on the surface. One such diameter will be the smallest for an irregular particle and one such diameter will be the largest. The center of mass for a sphere is the center of the sphere, provided that the sphere is uniform. For a sphere the diameter should pass through the center of the sphere.

According to one embodiment of the first aspect the porous particle comprises at least one selected from the group consisting of agarose, silica, cellulose, poly vinyl alcohols, polyethylene glycols, polystyrene, and derivatives thereof. Specific but non-limiting examples of particle materials are given in the working examples.

According to one embodiment of the first aspect the magnetic particles comprise at least one magnetic material chosen from magnetic metals, magnetic metal alloys and magnetic oxides or combinations thereof. Non-limiting examples include iron, nickel, cobalt, gadolinium, neodymium and samarium, as well as oxides and alloys thereof.

In one embodiment of the first aspect the magnetic particles have a density which is higher than the density of the non-magnetic porous particle. Thus the magnetic particles can be used to increase the density of the entire particles. This can be useful if gravity or centrifugation should be used for separating the particles during any process.

Suitable magnetic particles can be roughly divided into three groups:

Solid magnetic microparticles. These frequently have low magnetic force, and low capacity. They are currently less suitable for use in the process and system disclosed herein. Examples include Dynabeads® (Dynal/Invitrogen Co.) and Micromer® M (magnetic polystyrene particles from Micromod Partikeltechnologie GmbH, Rostock, Germany).

Porous magnetic particles. These have good magnetic properties and high capacity. They are suitable for use in the process and system disclosed herein. Examples include the Mag Sepharose particles from GE Healthcare Life Sciences, Biovision, Inc, PureCube MagBeads from Cube Biotech, and particles produced as outlined in the present description and described in detail in the co-pending international application claiming priority from SE 1351038-3, filed on Sep. 9, 2013.

Solid magnetic particles, for example the Cobalt particles (TurboBeads® product range from Turbobeads LLC, Zürich, CH) and similar, having high magnetic force.

In one embodiment the functional groups on the surface of the porous particle are at least one selected from the group consisting of —SH, —S—S-pyridin, —COOH, —NH$_2$, —CHO, —OH, phenol, anhydride, epoxy, S—Au, amide, amino ethyl, diethyl aminoethyl, quaternary aminoethyl, carboxymethyl, phosphopropyl and sulfopropyl.

In one embodiment at least one selected from the at least one type of functional groups on the exterior and interior surfaces the porous particle and the at least one type of functional groups on the surface of the magnetic particles comprise complex binding groups. In one embodiment the complex binding groups is at least one selected from the group consisting of IDA (Imminodiacetate) and derivatives thereof, TED (tris(carboxymethyl) ethylenediamine) and derivatives thereof, CM-Asp (Carboxymetylated aspartic acid) and derivatives thereof, NTA (nitrilotriacetic acid) and derivatives thereof, TREN (tris(2-aminoethyl) amine) and derivatives thereof, DPA (dipicolylamine) and derivatives thereof, C6-S gel (hexylsulfido groups) and derivatives thereof, EDTA (Etylene diamine tetraacetate) and derivatives thereof. These complex binding structures can bind for instance metal ions which in turn can interact with a peptide chain comprising histidine. If antibodies comprising a histidine chain or tag are to be purified such groups are suitable to use.

In one embodiment at least one selected from the at least one type of functional groups on the exterior and interior surfaces the porous particle and the at least one type of functional groups on the surface of the magnetic particles (Mp) comprise hydrophobic groups. In one embodiment the hydrophobic groups are at least one selected from the group consisting of CnHm (1≤n≤20 4≤m≤42), phenol and derivatives thereof, thiophenol and derivatives thereof, and mercaptopyridine and derivatives thereof. Such hydrophobic groups are suitable if the particles are to be used in applications similar to hydrophobic chromatography. CnHm (1≤n≤20 4≤m≤42) is a general formula for many different organic compounds including but not limited to alkanes CnH2n+2.

In one embodiment the functional groups on the surface of the porous particle (Pp) is at least one which is the result of a reaction with at least one compound selected from the group consisting of divinylsulfone, benzoquinone, imidazol, periodate, trichloro-S-triazine, tosylate, diazonium, isourea salts, carbodiimides, hydrazine, epichlorohydrin, glutaraldehyd, cyanogenbromide, carbonylimidazol, N-hydroxysuccinimid, silanes and derivatives thereof.

In one embodiment the functional groups on the magnetic particles are at least one selected from the group consisting of —SH, —S—S-pyridin, —COOH, —NH$_2$, —CHO, —OH, phenol, anhydride, epoxy, S—Au, amide, amino ethyl, diethyl aminoethyl, quaternary am inoethyl, carboxymethyl, phosphopropyl and sulfopropyl.

In one embodiment the functional groups on the surface of the magnetic particles are at least one which is the result of a reaction with at least one compound selected from the group consisting of divinylsulfone, benzoquinone, imidazol, periodate, trichloro-S-triazine, tosylchloride, diazonium, isourea salts, carbodiimides, and silanes.

The chemical groups on the magnetic particles and on the non-magnetic porous particles are adapted so that a reaction can occur between chemical groups on the magnetic particles and chemical groups on the non-magnetic porous particles. Thus one functional group which is suitable for reaction with another functional group can be attached to the non-magnetic porous particle and a suitable corresponding functional group can be attached to the magnetic particles. One functional group can be attached either to the non-magnetic porous particle or to the magnetic particles as long as there is a suitable functional group on the other particle with which it can react. In one embodiment different several chemical groups are attached to the non-magnetic porous particle and different types of magnetic particles with corresponding different types suitable functional groups are attached to the different functional groups on the porous particle.

In one embodiment of the first aspect molecules adapted for molecular interactions are introduced on at least one selected from the group consisting of the porous particles and the magnetic particles. In one embodiment of the first aspect the molecules adapted for molecular interaction is at least one selected from the group consisting of an organic molecule, a protein, an antigen, an enzyme, an enzyme inhibitor, a cofactor, a hormone, a toxin, a vitamin, a glycoconjugate, a nucleic acid, a lectin, and a carbohydrate.

In one embodiment of the first aspect molecules adapted for detection are introduced on at least one selected from the group consisting of the porous particles and the magnetic particles. In one embodiment of the first aspect the molecules adapted for detection is at least one selected from the group consisting of an organic molecule, a protein, a nucleic acid and a lectin.

In one embodiment of the first aspect the magnetic particles comprise particles of at least one magnetic material embedded in a polymer matrix, and wherein said polymer matrix comprises the functional groups.

In a second aspect there is provided a particle, said particles comprise a non-magnetic porous particle, wherein the porous particle comprises pores, wherein the porous particle comprises at least one polymer, wherein the porous particle has at least one magnetic particle covalently bound to its surface, wherein the smallest diameter of the magnetic particles is larger than the average diameter of the pores of the porous particle.

In one embodiment of the second aspect the porous particle comprises at least one selected from the group consisting of agarose, silica, cellulose, polyvinyl alcohols, polyethylene glycols, polystyrene, and derivatives thereof.

The magnetic particles comprise at least one magnetic material, for example but not limited to magnetic metals, magnetic metal alloys, and magnetic oxides or combinations thereof.

In one embodiment the magnetic particles have a density which is higher than the density of the non-magnetic porous particle. The density is measured according to ISO 1183-1: 2012.

In one embodiment at least one of the porous particle and the at least one magnetic particle comprise molecules adapted for molecular interactions. A molecule adapted for interaction is a molecule with the ability to interact with another molecule by means including but not limited to forming a bond with another molecule.

In one embodiment at least one of the porous particle and/or the at least one magnetic particle comprise molecules adapted for detection.

In one embodiment the molecules adapted for detection is at least one selected from the group consisting of an organic molecules, a nucleic acid, an antigen, an enzyme, an enzyme inhibitor, a cofactor, a hormone, a toxin, a glycoconjugate, a lectin, and a carbohydrate. A molecule adapted for detection is a molecule which can be detected by any means. Examples include molecules which irradiate light of at least one specific wavelength.

In one embodiment the magnetic particles comprise particles of at least one material embedded in a polymer matrix, and wherein said polymer matrix comprises the functional groups. Examples of materials in the magnetic particles include but are not limited to magnetic metals, magnetic metal alloys, and magnetic oxides, such as iron, cobalt, and oxides thereof.

Herein is also provided a method for performing an assay comprising use of particles as described in the second aspect, said method comprising the steps of: a) contacting the particles with at least one analyte to be analyzed, b) exposing the particles to at least one selected from the group consisting of i) a magnetic field, ii) gravity, and iii) centrifugation, and c) reading a detectable signal from the particles.

According to one embodiment the assay is for diagnostic purposes in vitro. The particles disclosed herein also make it possible to construct multiplex reaction and/or analysis systems.

A multiplex assay is constructed using porous particles and magnetic particles as disclosed herein. Magnetic particles are supplied in a number of different sizes, and by coupling magnetic particles having a first diameter to one subgroup of porous particles, and magnetic particles having a second diameter, different from said first diameter, to a second subgroup, two batches of particles with distinct properties are obtained.

The agarose particles are divided into two batches. Magnetic particles having an average diameter of 10 µm are covalently bound to the agarose particles in the first batch according to the methods disclosed herein, producing a first group of particles called particle A. An antibody which binds specifically to a first analyte A is attached to the particles in this group. The second batch of agarose particles is reacted with magnetic particles having an average diameter of 2 µm, resulting in a second group of particles having covalently bound magnetic particles named B. A second antibody binding specifically to a second analyte B is attached to the particles in this second group named B.

The two groups of particles are brought in contact with a sample under conditions required for binding between antibody and analyte. The different size of the magnetic particles bound to the agarose particles can be used to discriminate between the two groups of particles, together with the analyte bound thereto. The two groups of particles can also be labeled with different labels representing different colors or combinations of different colors, for example but not limited to fluorescent labels.

If analyte A is present in the sample, this analyte will be bound to the first group of particles. If analyte B is not present it will not bind either to particle A or B.

In the next step the particles are rinsed to eliminate excess of analyte A or B. In the following step the particles are brought in contact with a surface on which analyte A and B are covalently immobilized. Since analyte A is bound to the particles from group A on which antibodies against analyte A are present, those particles will not stick to the surface. The absence of particles from group A on the surface indicates that analyte A is present in the sample.

Particles B on the other hand will stick to the surface since no analyte B is present in the sample and then anti-B will react with analyte B on the surface An alternative example is to use Particle A and Particle B where particle A has a certain bar code represented by e.g. a blue color and anti-A antibodies on the surface of the particle and particle B with e.g. a yellow color with anti-B antibodies on the surface.

The two particles A and B are brought in contact with a sample containing analyte A but not B. After rinsing the beads which is easy to perform since the particles are magnetic the particles are brought in contact with a solution containing anti-A antibodies provided with biotin and anti-B antibodies provided with biotin. After a second rinsing the beads are brought in contact with avidin provided with a fluorescent e.g. green color. A third rinsing is preformed and then the particles are examined. If the particles with green color are detected on the blue particles A then it is determined that analyte A is present in the sample.

Particles with no green fluorescence together with the characteristic bar code which indicate which analytes are not present in the sample The particles A and B can easily be discriminated from each other either based on their different size of the magnetic particles or different colors or fluorescent colors.

The above is equally applicable to three or more groups, provided that the magnetic particles have different size or bar codes. Particles having average diameters of 2, 5 and 10 µm can be used. The magnetic particles can also have different colors or combinations of colors and other distinguishable properties.

It should be noted that the aspects and embodiments disclosed herein are freely combinable unless otherwise defined.

EXAMPLES

Example 1. Preparation of Epoxide Activated Agarose Particles

Figure 2:
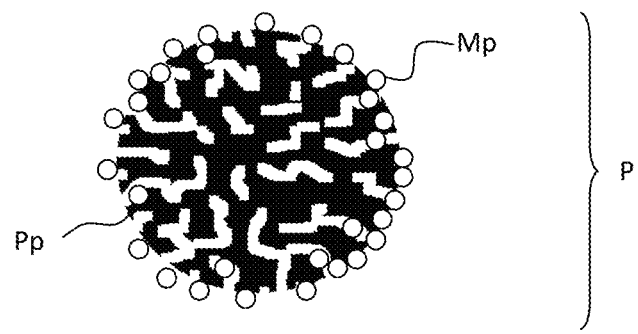
FIG. 2 schematically shows the cross-section of a similar particle (P) comprising a non-magnetic porous particle (Pp) with magnetic particles (Mp) which, depending on their size in relation to the diameter of the pores in the porous particle, have penetrated to a lesser or greater extent into said particle.

Sepharose 4B (GE Healthcare Life Sciences) was washed with distilled water on a glass filter and sucked dry. 3 g dry gel particles were suspended in 2.4 ml 1M sodium hydroxide solution and epichlorohydrin 0.45 ml was added drop wise under stirring at room temperature. The temperature was increased to 60° C. and maintained for 2 hours. The epoxide activated sepharose gel was washed with distilled water until neutral on a glass filter and finally re-suspended in distilled water, 50% gel concentration. The product constitutes one example of porous particles as defined herein, see e.g. the particles Pp in FIGS. 1 and 2.

Example 2. Production of Agarose Particles Decorated with Magnetic Particles Including One Size of Magnetic Particles Commercially available magnetic microparticles with amino ($NH_2$) functionality in the sizes from 2 µm to 10 µm were used in these investigations as the magnetic material. These particles are examples of magnetic particles as defined herein, see e.g. the magnetic particles Mp in FIGS. 1 and 2.

The magnetic particles Micromer® M-$NH_2$ (2 µm and 10 µm) were separately covalently attached to porous epoxide-activated agarose particles as follows. Micromer® -M-$NH_2$ (250 µL, $7\times10^8$ particles/ml), from Micromod Partikelteknologie GmbH, was washed twice in 1000 µL PBS (15 mM phosphate, 150 mM NaCl, pH 7.4) and re-suspended in 1000 µL PBS. The epoxide activated agarose particles, 1 ml settled gel, were re-suspended in 10 ml 0.01M NaOH solution, added to the magnetic particle suspension and reacted for 12 hours for the 2 µm particles and for 30 minutes for the 10 µm particles at room temperature on vortex.

Figure 3:
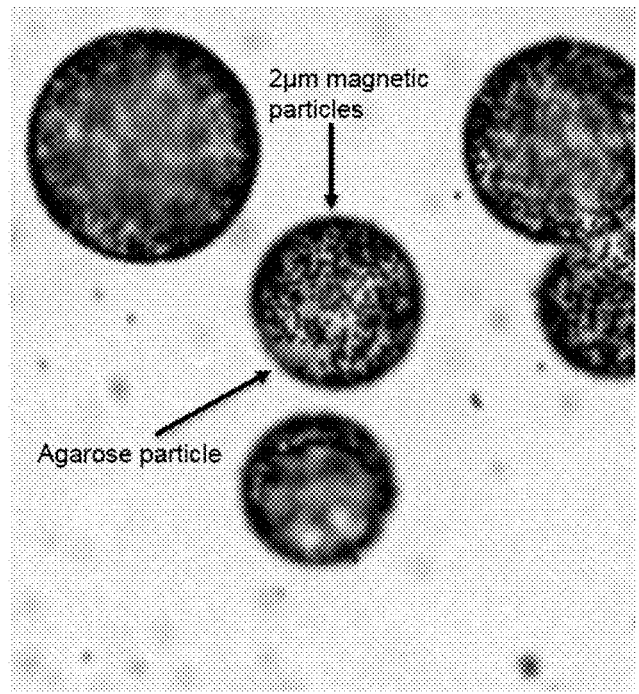
FIG. 3 shows an optical microscope image of agarose beads as porous particles with smaller magnetic particles bound to their surface, resulting from a reaction between epoxide-activated agarose and Micromer® M $NH_2$ particles having the size of 2 µm (magnetic polystyrene particles from Micromod Partikeltechnologie GmbH, Rostock, Germany).
Figure 4:
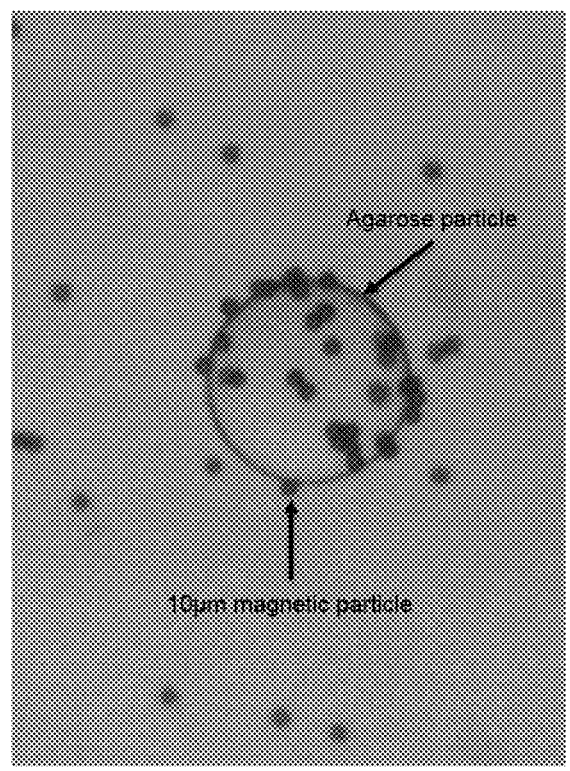
FIG. 4 shows an optical microscope image of magnetic agarose particles resulting from the reaction between epoxide-activated agarose and 10 µm Micromer® M $NH_2$ particles.

Excess magnetic particles with amino functionality were removed on a sintered filter funnel with 50 ml 10 mM sodium phosphate buffer pH 7.4 resulting in a solution with agarose particles decorated with 2 µm or 10 µm magnetic particles as shown in FIG. 3 and FIG. 4, respectively. These particles are an example of particles as defined herein, and as schematically shown as the particles P in FIGS. 1 and 2.

Example 3. Production of Agarose Particles Decorated with Magnetic Particles Including Two Sizes of Magnetic Particles The magnetic particles Micromer® M-$NH_2$ (5 µm and 10 µm) were covalently attached to porous epoxide-activated agarose particles as follows:

First, 10 µm Micromer® -M-$NH_2$ (250 µL, $7\times10^8$ particles/ml), from Micromod Partikelteknologie GmbH, was washed twice in 1000 µL PBS (15 mM phosphate, 150 mM NaCl, pH 7.4) and re-suspended in 1000 µL PBS. The epoxide activated agarose particles, 1 ml settled gel, were re-suspended in 10 ml 0.01M NaOH solution, added to the 10 µm magnetic particle suspension and reacted for 30 minutes at room temperature on vortex.

Second, 5 µm Micromer® -M-$NH_2$ (250 µL, $7\times10^8$ particles/ml), from Micromod Partikelteknologie GmbH, was washed twice in 1000 µL PBS (15 mM phosphate, 150 mM NaCl, pH 7.4) and re-suspended in 1000 µL PBS. Then the 5 µm magnetic particles were added to the agarose 10 µm magnetic particle suspension and reacted for 30 minutes at room temperature on vortex.

Figure 5:
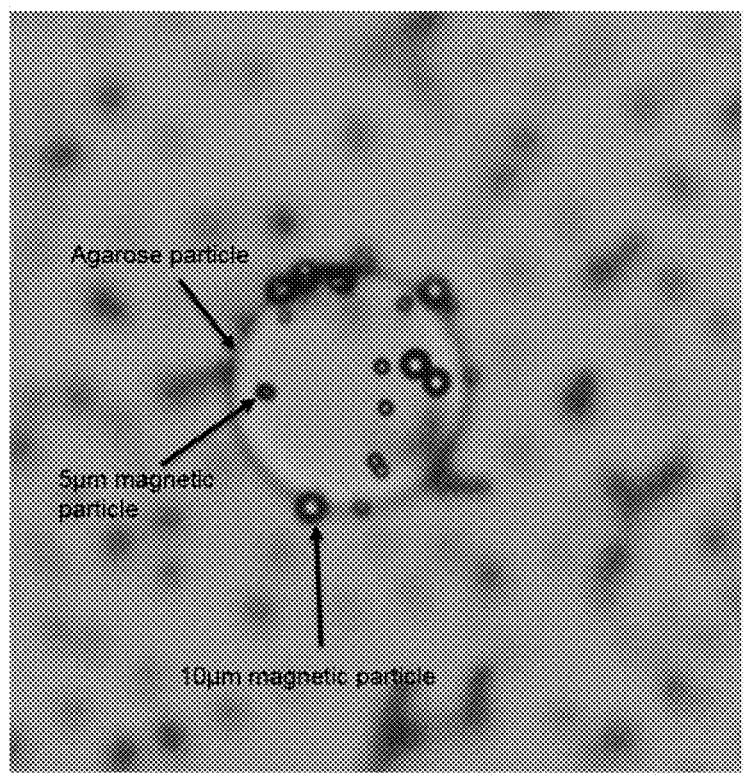
FIG. 5 shows an optical microscope image of magnetic agarose particles including two different sizes of magnetic particles, resulting from the reaction between epoxide-activated agarose and 10 µm Micromer® M $NH_2$ particles followed by reaction with 5 µm Micromer® M $NH_2$ particles.

Excess magnetic particles were removed on a sintered filter funnel with 50 ml 10 mM sodium phosphate buffer pH 7.4 resulting in a solution with agarose particles decorated with 5 µm and 10 µm magnetic particles as shown in FIG. 5.

Example 4. Production of Agarose Particles Decorated with Magnetic Particles Including Three Sizes of Magnetic Particles The magnetic particles Micromer® M-$NH_2$ (2 µm, 5 µm and 10 µm) were covalently attached to porous epoxide-activated agarose particles as follows:

First, 10 µm Micromer® -M-$NH_2$ (250 µL, $7\times10^8$ particles/ml), from Micromod Partikelteknologie GmbH, was washed twice in 1000 µL PBS (15 mM phosphate, 150 mM NaCl, pH 7.4) and re-suspended in 1000 µL PBS. The epoxide activated agarose particles, 1 ml settled gel, were re-suspended in 10 ml 0.01M NaOH solution, added to the 10 µm magnetic particle suspension and reacted for 30 minutes at room temperature on vortex.

Second, 5 µm Micromer® -M-$NH_2$ (250 µL, $7\times10^8$ particles/ml), from Micromod Partikelteknologie GmbH, was washed twice in 1000 µL PBS (15 mM phosphate, 150 mM NaCl, pH 7.4) and re-suspended in 1000 µL PBS. Then the 5 µm magnetic particles were added to the agarose 10 µm magnetic particle suspension and reacted for 30 minutes at room temperature on vortex.

Third, 2 µm Micromer® -M-$NH_2$ (250 µL, $7\times10^8$ particles/ml), from Micromod Partikelteknologie GmbH, was washed twice in 1000 µL PBS (15 mM phosphate, 150 mM NaCl, pH 7.4) and re-suspended in 1000 µL PBS. Then the 2 µm magnetic particles were added to the agarose 10 µm/5 µm magnetic particle suspension and reacted for 30 minutes at room temperature on vortex.

Figure 6:
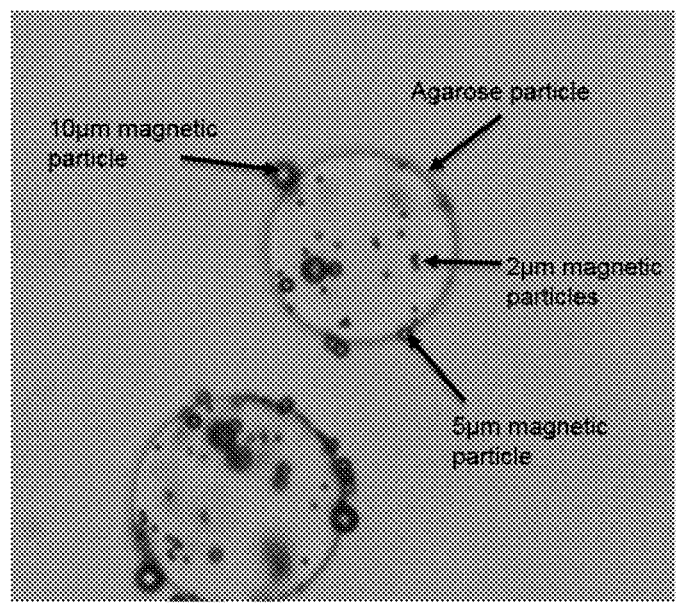
FIG. 6 shows an optical microscope image of magnetic agarose particles including three different sizes of magnetic particles, resulting from the reaction between epoxide-activated agarose and 10 µm Micromer® M $NH_2$ particles followed by reaction with 5 µm Micromer® M $NH_2$ particles and further by reaction with 2 µm Micromer® M $NH_2$ particles.
Figure 7:
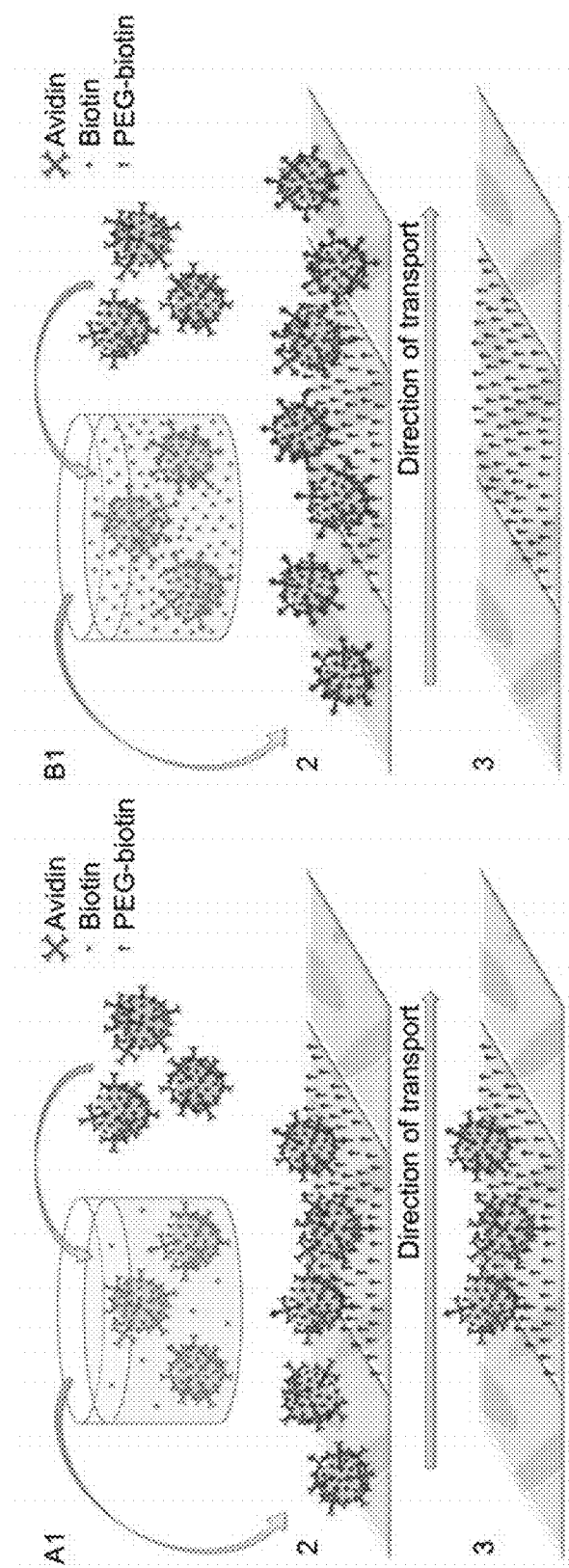
FIG. 7 shows an example of how particles (P) are capturing analytes present in the patient sample in case A or not in case B. If the analyte is present in the sample the particles (P) with a characteristic color and size of the magnetic particles (Mp) will not stick to the surface. If the analyte is not present the particles (P) will stick. This is just an example and other combinations which will result in other outcomes are possible.

Excess magnetic particles were removed on a sintered filter funnel with 50 ml 10 mM sodium phosphate buffer pH 7.4 resulting in a solution with agarose particles decorated with 2 µm, 5 µm and 10 µm magnetic particles as shown in FIG. 6.

Example 5. Immobilization of Thiolated Protein A to Magnetic Agarose Particles Approximately 60 µl settled magnetic agarose particles (2 µm) were pipetted into a 1.5 ml Eppendorf tube. The magnetic agarose particles were attracted to the wall of the Eppendorf tube by a permanent magnet and the solution was removed and the particles were re-suspended in 1 ml solution of thiolated protein A (1 mg/ml in 15 mM phosphate buffer pH 8). After 1 hour reaction at room temperature and by gentle mixing the supernatant was collected by separation of the particles from the solution by a permanent magnet. The content of protein A in the supernatant was evaluated with Uv/Vis spectroscopy by measuring the absorbance at 280 nm (A280 nm), see Table 1.

TABLE 1

Evaluation of the ligand concentration of protein A
on to magnetic agarose particles by measuring
the absorbance at 280 nm on the supernatant.

| Sample | Absorbance, 280 nm $A_{280\,nm}$ |
|---|---|
| Protein A 0 mg/ml | 0.001 |
| Protein A 0.5 mg/ml | 0.142 |
| Protein A 1.0 mg/ml | 0.274 |
| Supernatant, Protein A + magnetic agarose particles | 0.166 |

The content of protein A on the 60 μl particles was determined by subtracting the content of protein A in the supernatant (0.6 mg/ml) from the content in the added protein A solution (1 mg/ml). The extent of protein A labeling was determined to be around 6.5 mg/ml settled magnetic particles.

Example 6. Multiplex Analysis Using Porous Particles Carrying Magnetic Particles of Different Sizes Detection of presence of human serum albumin (HSA) and Immunoglobulin G (IgG) and absence of lysozyme in a sample mixture was performed by using magnetic particles comprising porous particles decorated with magnetic particles with different sizes. The magnetic particles were produced as in Example 2 with different magnetic particle sizes yielding magnetic particles as in FIG. 3 and FIG. 4. The inner volume of the particles decorated with 2 μm magnetic particles was covalently coupled with anti-HSA yielding anti-HSA-2 μm-magnetic particles.

In a similar fashion anti-IgG-5 μm-magnetic particles and anti-lysozyme-10 μm-magnetic particles were produced. The 2 μm-magnetic particles, the 5 μm-magnetic particles and the 10 μm-magnetic particles are easy to distinguish in an optical microscope as the unique magnetic decoration comprises particles with different sizes.

The particles were added to a protein mixture (1 ml) containing IgG and HSA both labeled with fluorescein isothiocyanate (FITC), and incubated at room temperature with gentle mixing. After 15 minutes the magnetic particles were washed with 5×1 ml PBS by the use of magnetic separation to remove unbound material from the magnetic particle suspension. The magnetic particles were re-suspended in 250 μl PBS and visualized under a fluorescence microscope. Fluorescence from FITC was observed on the 2 μm-magnetic particles and on the 5 μm-magnetic particles whereas the 10 μm-magnetic particles did not show any fluorescence which indicates the presence of HSA and IgG and the absence of lysozyme in the sample mixture.

The use of the described magnetic agarose particles comprising different magnetic particle sizes eliminates the need of three different fluorophores for detection as just one fluorophore is used in the above experiment.

By using three different sizes of magnetic particles, which are easy to distinguish between in an optical microscope, the agarose particles can be "decorated" with the following six (6) combinations. These have been produced and have subsequently been used as barcodes in a multiplex analysis assay:

Barcode No. 1, agarose particle comprising 2 μm magnetic particles, FIG. 3.
Barcode No. 2, agarose particle comprising 5 μm magnetic particles.
Barcode No. 3, agarose particle comprising 10 μm magnetic particles, FIG. 4.
Barcode No. 4, agarose particle comprising 2 μm and 10 μm magnetic particles.
Barcode No. 5, agarose particle comprising 2 μm, 5 μm and 10 μm magnetic particles, FIG. 6.
Barcode No. 6, agarose particle comprising 5 μm and 10 μm magnetic particles, FIG. 5.

Thus, simple and yet reliable and easily distinguishable codes or fingerprints can be achieved using the methods described herein.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The invention claimed is:

1. A method for performing an assay using a plurality of particles, each particle of the plurality of particles comprising a non-magnetic porous particle having an exterior surface, pores and an interior surface defined by said pores, the porous particle comprising at least one polymer, said particle having at least one magnetic particle covalently bound to the outer parts thereof, wherein the smallest diameter of at least 95 percent per weight of all magnetic particles is larger than the largest diameter of at least 95% of the pores of the porous particles, wherein a fraction of the magnetic particles have a diameter such that they enter the non-magnetic porous particle, and wherein said at least one magnetic particle constitutes a feature capable of distinguishing one group of particles from another, the method comprising the steps of:
   contacting the plurality of particles with a sample comprising at least one analyte to be analysed wherein the particles have an affinity for said analyte,
   bringing the plurality of particles in contact with a surface on which molecules which have bioaffinity for the analyte immobilised to the particle are immobilized,
   exposing the plurality of particles to at least one of i) a magnetic field, ii) gravity, and iii) centrifugation followed by rinsing the surface from non-specifically bound particles, and
   reading a detectable signal from the plurality of particles which are immobilised to a surface.

2. The method according to claim 1, wherein the assay is an in vitro assay for diagnostic purposes.

3. The method according to claim 1, wherein the assay is a multiplex assay involving the use of subgroups of particles wherein the porous particles in each subgroup carry magnetic particles of different size.

4. The method according to claim 1, wherein the assay is a multiplex assay involving the use of subgroups of particles wherein the porous particles in each sub-group carry magnetic particles of different color, combination of different colors and or size.

5. The method according to claim 1, wherein the porous particle comprises at least one material selected from the group consisting of agarose, silica, cellulose, polyvinyl alcohols, polyethylene glycols, polystyrene, and derivatives thereof.

* * * * *